US007921021B1

(12) United States Patent  (10) Patent No.: US 7,921,021 B1
Newman  (45) Date of Patent: Apr. 5, 2011

(54) SYSTEM, METHOD, AND MANUFACTURE FOR DECREASING THE AMOUNT OF TREATMENT A PATIENT REQUIRES FROM A FIRST CARE-GIVER

(75) Inventor: Fred Newman, Houston, TX (US)

(73) Assignee: Interface EAP, Inc., Houston, TX (US)

( * ) Notice: Subject to any disclaimer, the term of this patent is extended or adjusted under 35 U.S.C. 154(b) by 1309 days.

(21) Appl. No.: 11/212,081

(22) Filed: Aug. 24, 2005

Related U.S. Application Data

(60) Provisional application No. 60/604,633, filed on Aug. 26, 2004.

(51) Int. Cl.
*G06F 19/00* (2006.01)
(52) U.S. Cl. .......................................................... 705/3
(58) Field of Classification Search .................. 705/2, 3, 705/4
See application file for complete search history.

(56) References Cited

U.S. PATENT DOCUMENTS

| 6,338,039 B1 * | 1/2002 | Lonski et al. ...................... 705/3 |
| 2002/0004725 A1 * | 1/2002 | Martin et al. ...................... 705/2 |
| 2002/0192159 A1 * | 12/2002 | Reitberg ......................... 424/9.1 |
| 2003/0120516 A1 * | 6/2003 | Perednia ........................... 705/3 |
| 2003/0144884 A1 * | 7/2003 | Mayaud ............................ 705/3 |

OTHER PUBLICATIONS

Joyce Kamanitz, Anthony Kotin, Norrie Thomas; Use of Pharmacy Claims Data to Improve Mental Health Disease Management; Drug Benefit Trends; p. 214, 215, 219, 221 and 222.

A Holistic Way to Cut Your Antidepressant Drug Costs; Managing Benefits Plans; Mar. 2006; p. 1-4; Issue 06-03; Institute of Management & Administration, Inc.; New York, U.S.
Nancy Ann Jeffrey, HMOs Seek Cures for Costly Psychosomatic Ills, The Wall Street Journal, Jul. 9, 1997, Section B1.
Craig Gunsauley, Prozac Nation: As anti-depressant utilization surges, PBMs promote various programs, Employee Benefit News, Mar. 1, 2002, vol. 16, No. 3.
Unknown, Stress Should Be Targeted in Assessments for Disease Risk, BenefitNews.com, Mar. 27, 2003.
Unknown, Ohio Insurer Offers Depression Management Program, BenefitNews.com, Aug. 12, 2003.
Unknown, Woman Say Depression Hampers Ability to Work, BenefitNews.com, Nov. 11, 2003.
Unknown, Let the Sun Shine in: Medication, Talk Therapy Solutions Offer Help, Hope to Depression Sufferers, BenefitNews.com, Dec. 22, 2003.

(Continued)

*Primary Examiner* — Gerald J O'Connor
*Assistant Examiner* — John A Pauls
(74) *Attorney, Agent, or Firm* — Arnold & Knobloch, L.L.P.

(57) ABSTRACT

A process, system, and manufacture are provided for decreasing the amount of treatment a patient requires from a first care-giver. In at least one example, the system comprises a means for receiving a set of records, and the set of records includes at least one representing a treatment prescribed by the first care-giver, and at least one representing at least one patient characteristic. There is also a means for determining, from the set of records, independently of records relating to effectiveness of the treatment prescribed for the patient, and based on a predetermined set of screening criteria, whether a different treatment is appropriate. Further, a means is provided for generating, based on the screening, an eligibility tag associated with the patient for providing notice to the patient associated with the eligibility tag of the different treatment availability at no cost to the patient and of a financial consequence of receipt of the treatment.

20 Claims, 2 Drawing Sheets

OTHER PUBLICATIONS

Sara Schaefer Munoz, Cost to Treat a Depression Case Falls, The Wall Street Journal, Dec. 31, 2003, Health & Family.

Unknown, Treatment Costs Down, Yet Depression Still Cost Drain, BenefitNews.com, Jan. 6, 2004.

Unknown, Month-long Campaign Targets Depression, Heart Disease, BenefitNews.com, Feb. 5, 2004.

Unknown, Worsening Depression and Suicidality in Patients Being Treated with Antidepressant Medications, U.S. Food and Drug Administration, FDA Public Health Advisory, Mar. 22, 2004.

Unknown, Depressed Employees Underuse Mental Health Benefits, BenefitNews.com, Mar. 30, 2004.

Unknown, Employers Need to be Aware of Presenteeism's Cost, BenefitNews.com, Apr. 27, 2004.

Unknown, More Than a Quarter of Americans Treated for Mental Health, BenefitNews.com, May 6, 2004.

Unknown, Prescription Drug Use Soars Nationally, BenefitNews.com, Dec. 7, 2004.

David P. Steiner, Private Sector Needs Help to Rein in Health Care Costs, Houston Chronicle, Jan. 10, 2005.

Unknown, Companies Tackle Root Causes of Health Care Cost Increases, BenefitNews.com, May 24, 2005.

Barbara Martinez, Drug Co-Pays Hit $100 to Curb Rising Costs, Companies Try Range of Tactics to Push Employees to Cheaper Medicines, The Wall Street Journal, Jun. 28, 2005, D1.

Anna Wilde Mathews and Heather Won Tesoriero, FDA Moves Toward Harder Line on Suicide Risks, The Wall Street Journal, Jul. 1, 2005, B3.

Jennifer Corbett Dooren, FDA to Boost ADHD Drug Warnings, Dow Jones Newswires, Jul. 1, 2005, B3.

Leila Abboud, The Next Phase in Psychiatry, The Wall Street Journal, Jul. 27, 2005, D1.

Anna Wilde Mathews, Reading Fine Print, Insurers Question Studies of Drugs, The Wall Street Journal, Aug. 24, 2005, A1.

Leila Abboud, Generic Fares Well in Big Psychiatry Study, The Wall Street Journal, Sep. 20, 2005, D1.

Armstrong, David and Winstein, Keith J.; Antidepressants Under Scrutiny Over Efficacy; Reprinted from The Wall Street Journal, Jan. 17, 2008; 2 pages.

Brauer, Lisa PhD; Measurement-Based Outcome for Depression; Clinical Compass, Jan. 13, 2009, vol. 4, Issue 1, 3 pages.

Centers for Prevention and Health Services; An Employer's Guide to Behavioral Health Services, 14 pages.

Dooren, Jennifer Corbett; Effectiveness of Antidepressants Varies Widely; Reprinted from The Wall Street Journal, Jan. 6, 2010; 1 page.

Koster, Kathleen; Study finds antidepressants provide no cure for absenteeism; EmployeeBenefit news; Feb. 16, 2010, 1 page.

Wang, Shirley S.; Studies: Mental Ills Are Often Overtreated or Undertreated; Reprinted from The Wall Street Journal, Jan. 5, 2010; 1 page.

Wojcik, Joanne; Antidepressant monitoring falls short: Study; Business Insurance; Aug. 9, 2000; 1 page.

Department of Labor Request for Ruling: Pharmacy Intervention Protocol (patent pending), Interface EAP, 17 pages.

Letter from Cribbs Rizza, Elaine at The Rizza Group Professional Corporation regarding Total Life Assistance, Jul. 7, 2005, 3 pages.

Letter from Cribbs Rizza, Elaine at The Rizza Group Professional Corporation regarding Total Life Assistance, Apr. 26, 2006, 9 pages.

Letter from Hoffman, Michael at Arizona Benefit Plans, Inc. regarding Existing Large Employer utilizing the Pharmacy Intervention Protocol, Aug. 19, 2010, 1 page.

Fax from Mitchell, Heather at U.S. Department of Labor regarding rules of wellness program, Jun. 24, 2010, 4 pages.

Fax from Farrington, Christina at The Phia Group, LLC regarding comparison of wellness and pharmacy review program, Jul. 9, 2010, 3 pages.

Newman, Fred, Improving Treatment Outcomes through Drug Interventions, Journal of Employee Assistance, 2nd Quarter, 2010, 3 pages.

Case Study—Interface EAP's Pharmacy Intervention Protocol, 3 pages.

* cited by examiner

SYSTEM, METHOD, AND MANUFACTURE FOR DECREASING THE AMOUNT OF TREATMENT A PATIENT REQUIRES FROM A FIRST CARE-GIVER

This application claims the benefit of U.S. Provisional Application No. 60/604,633, filed Aug. 26, 2004, and incorporated herein by reference.

BACKGROUND OF THE INVENTION

For most employers at any given time, between 10% and 20% of employees and dependents are facing a variety of issues that can create symptoms of stress, anxiety, and/or depression. How they handle these symptoms will have a direct effect not only on their personal lives, but also on their labor costs (through job performance issues, disability claims, increased utilization of medical services, and the cost of prescription drugs). The assistance and treatment that those experiencing these issues receive will determine the financial impact to the employer.

In the past five years, health care costs have risen more than 50%, with annual increases of 13% to 14% in 2001 and 2002. Disability claims for stress and depression are on the rise. Productivity is being negatively impacted.

As reported in the Wall Street Journal, a study published by the Health Enhancement Research Organization surveyed over 46,000 workers at six major U.S. employers and reported that over 20% of all employees screened as highly stressed or depressed, and their medical claims averaged almost 49% more than the other 80% (not in that identified group). Drug trend reports underscore the problem of antidepressants. They are the most-utilized class of all prescription drugs and the second-highest drug expenditure category. The Dec. 21, 2003, Wall Street Journal reports that pharmaceutical costs for depression increased 425% from 1990 to 2000 while, during the same period, inpatient costs decreased 33.6% and outpatient costs increased 46.9%. As employers look for ways to cut costs, mental health benefits become an easy target.

Consider these facts from Prozac Nation, Employee Benefit News (2002):

New research shows that the number of Americans receiving treatment for depression soared nearly four-fold between 1987 and 1997, from 1.7 million to 6.3 million.

In terms of revenue, three of the top eleven prescription drugs in the year 2000 were antidepressants.

The article also stated the following:

"Many patients seek treatment for a short-term and end up with long-term drug therapy.

"We know that 50% to 60% of patients with depression receive their treatment from primary care physicians. Unfortunately, too many of these doctors don't have either the skills or the time to detect the presence of depression among their patients."

"The best treatment for major depression is a combination of drug therapy and psychotherapy, but many patients receive pills alone. Depression management programs should coordinate services through employee assistance programs ['EAPs'] and health care plans."

The overall results of a three-year study published by Abbott Laboratories reported that total healthcare costs averaged approximately $2,200.00 less per year for patients (and family members) whose mental health treatment was managed by an EAP vs. patients whose mental heath treatment was managed by a medical UR (standing for Utilization Review). The savings were realized even though patients in the EAP managed group averaged approximately $750.00 more pretreatment episode for mental health care than the patients managed by the medical UR. This study documents that it is actually more costly to suppress mental health care. Appropriate treatment is a cost savings tool. Stress, anxiety, and depression are increasing overall healthcare costs at a rate much greater than the costs of providing effective treatment. Add productivity and disability losses to the equation and the costs become even greater.

During the past five years, healthcare costs have risen more than fifty percent. Even with numerous valid studies documenting the impact and costs of mental health issues on labor costs (including healthcare), many employers, brokers, consultants, and TPAs (standing for Third Party Administrator) fail to realize the extent of the problem and, as a result, continue to oppose "mental health parity." While parity on its own is not the answer, the denial of the existence and impact of mental health issues among employees can be costly for the employer.

SUMMARY OF THE INVENTION

According to one example aspect of the invention, a system is provided for decreasing the amount of treatment a patient requires from a first care-giver. In at least one example, the system comprises a means for receiving a set of records, wherein the set of records comprises: at least one representing a treatment prescribed by the first care-giver, and at least one representing at least one patient characteristic. A means is also provided for determining, from the set of records, independently of records relating to effectiveness of the treatment prescribed for the patient, and based on a predetermined set of screening criteria, whether a different treatment is appropriate, and means is provided for generating, based on the screening, an eligibility tag associated with the patient. A further means provides a notice to the patient associated with the eligibility tag of the different treatment availability at no cost to the patient and of a financial consequence of receipt of the treatment.

In at least one example of such a system, the treatment prescribed by the first care-giver comprises a drug chosen from the group of: tricyclic antidepressants, anxiolytic hypnotics, non-benzodiazepines, bupropion, duloxetine, mirtazapine, nefazodone, trazodone, venlafaxine, sedative hypnotics, phenelzine, tranylcypromine, escitalopram, citalopram, fluoxetine, fluvoxamine, paroxetine, and/or sertraline.

In some examples of such a system, the first care-giver comprises a physician.

Further, in at least one example, the means for determining comprises a means for comparing a practice type of the physician prescribing a drug to the type of drug prescribed.

In some example systems, the means for providing a notice comprises a means for providing a description of a cost saving for the treatment prescribed by the first care-giver, wherein the cost savings is dependent upon participation by the patient in the different treatment, and the cost saving comprises a reduction in a cost (e.g., a co-pay component of an insurance policy) in the event of participation by the patient in the different treatment.

In alternative examples, the providing a notice comprises providing a description of a cost increase for the treatment prescribed by the first care-giver, wherein the cost increase is dependent upon lack of participation by the patient in the different treatment, and the cost increase comprises an increase in a cost (e.g., a co-pay) in the event of failure by a patient to participate in the different treatment.

In many systems, the different treatment comprises counseling and/or psychotherapy. In further examples, there is a monetary incentive to an employer to provide the different treatment.

At least one further example includes the additional step of educating the patient regarding the different treatment and follow up with the patient.

According to still a further aspect of the invention, a process is provided for decreasing the amount of treatment a patient requires from a first care-giver. The process comprises receiving a set of records wherein the set of records comprises: at least one representing a treatment prescribed by the first care-giver, and at least one representing at least one patient characteristic; determining, from the set of records, independently of records relating to effectiveness of the treatment prescribed for the patient, and based on a predetermined set of screening criteria, whether a different treatment is appropriate; generating, based on the screening, an eligibility tag associated with the patient; and providing a notice to the patient associated with the eligibility tag of the different treatment availability at no cost to the patient and of a financial consequence of receipt of the treatment.

In at least one example of such a process, the treatment prescribed by the first care-giver comprises a drug chosen from the group of: tricyclic antidepressants, anxiolytic hypnotics, non-benzodiazepines, bupropion, duloxetine, mirtazapine, nefazodone, trazodone, venlafaxine, sedative hypnotics, phenelzine, tranylcypromine, escitalopram, citalopram, fluoxetine, fluvoxamine, paroxetine, and/or sertraline.

In at least some such processes, the first care-giver comprises a physician.

In some examples, the determining comprises comparing a practice type of the physician prescribing a drug to the type of drug prescribed, and/or the providing a notice comprises providing a description of a cost saving for the treatment prescribed by the first care-giver, wherein the cost savings is dependent upon participation by the patient in the different treatment.

In some further examples, the cost saving comprises a reduction in a co-pay component of an insurance policy.

In an alternative example, the providing a notice comprises providing a description of a cost increase for the treatment prescribed by the first care-giver, wherein the cost increase is dependent upon lack of participation by the patient in the different treatment. For example, in some examples, there is an increase in a cost (e.g., a co-pay component of an insurance policy) in the event of failure by a patient to participate in the different treatment.

In some examples, the different treatment comprises counseling and/or psychotherapy. Still further examples of the process comprise educating the patient regarding the different treatment.

According to yet another aspect of the invention, a manufacture is provided comprising: a medium of recordation of records, a first recordation associated with the medium of a set of records (wherein the set of records comprises: at least one field representing a treatment prescribed by the first care-giver and at least one field representing at least one patient characteristic); a second recordation associated with the medium of at least one field associated an availability to a patient of a different treatment at no cost to the patient; and a third recordation associated with the medium of a financial consequence of receipt or rejection of the different treatment.

In yet a further embodiment, the medium comprises paper.

In still further examples, wherein the medium comprises a set of records.

In even further examples, the medium comprises a computer display.

In any event, the medium is, in various examples of the manufacture, a tangible medium and/or an intangible medium.

DETAILED DESCRIPTION OF EXAMPLES OF THE INVENTION

Figure 1A:
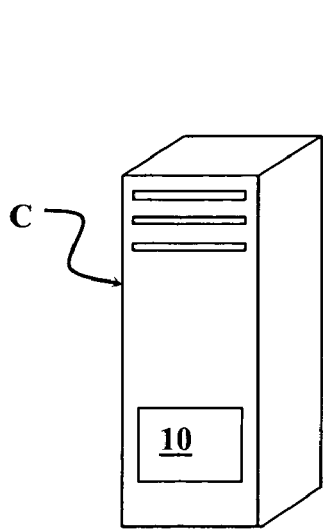
FIG. 1A is a perspective view of an example of a system useful according to some examples the present invention.
Figure 1B:
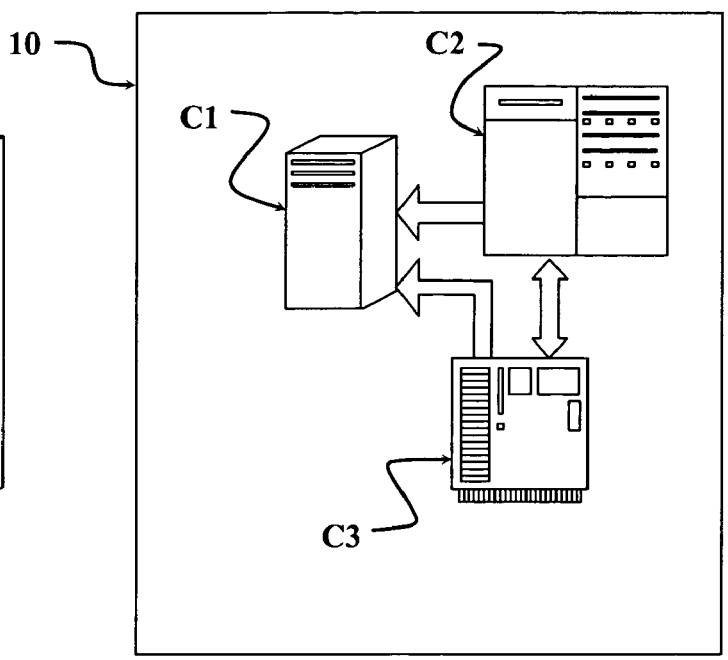
FIG. 1B is a diagram of another system useful according to further examples of the present invention.

Referring now to FIG. 1A, an example embodiment of the invention is seen in which a system 10 is provided for decreasing the amount of treatment a patient requires from a first care-giver. As shown, system 10 comprises a computer C. In an alternative example, seen in FIG. 1B, system 10 comprises a network of computers C1-C3, which are connected in any way known to those of skill in the art with any protocol known to those of skill in the art.

Figure 2:
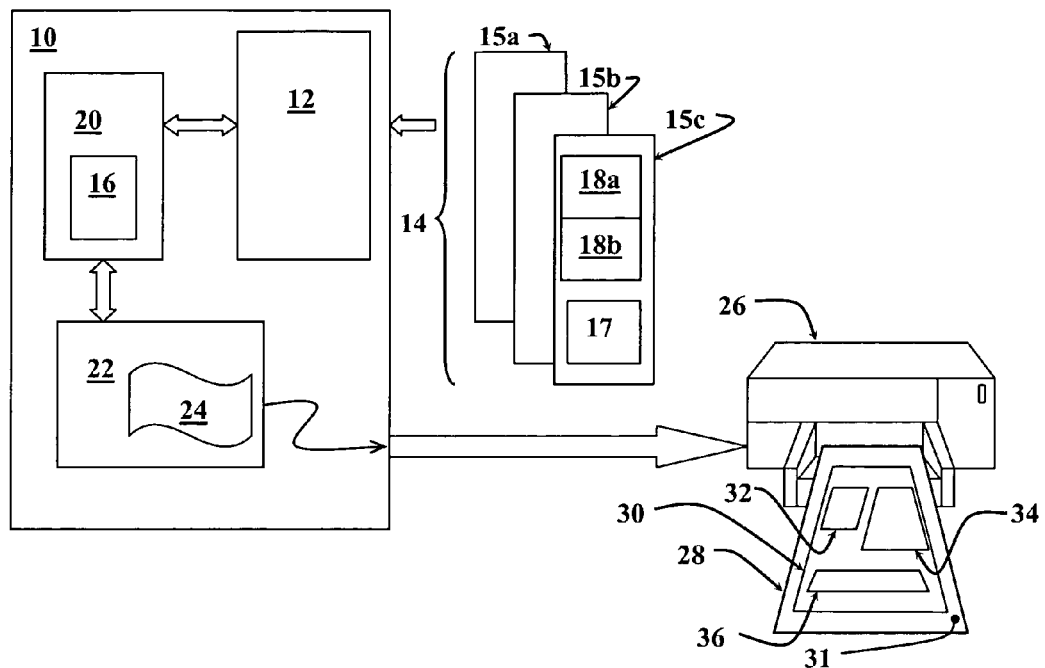
FIG. 2 is a representational view of various components of some examples of the invention.

As seen in FIG. 2, whatever the form of system 10, it comprises means 12 (e.g., a memory) for receiving a set 14 of records 15 (in the figure, 3 records 15a-15c are shown for simplicity; however, there is no limit according to the invention). In at least one example, any particular individual record 15 comprises at least one field 17, representing a treatment prescribed by the first care-giver, and at least one field 18, representing at least one patient characteristic. In some examples, the at least one characteristic comprises a medical history, in which case there would be a plurality of fields 18a, 18b, etc., in a record 15. Means 20 is provided for determining from the set 14 of records 15 (independently of records relating to effectiveness of the treatment prescribed for the patient and based on a predetermined set field 16 of screening criteria) whether a different treatment is appropriate. In at least one example, means 20 comprises an arithmetic logic unit coupled to a memory including the screening criteria field 16. At least one benefit of determining appropriateness independently of effectiveness is that patients who are responding well to the first treatment, which may be expensive, might be eligible for other treatment that would reduce the need for the expensive treatment.

Means 22 (for example, a "write" object in computer code) is provided for generating, based on the screening, an eligibility tag 24 associated with the patient; and means 26 (for example, a printer) provides a notice 28 to the patient associated with the eligibility tag 24 of the different treatment availability. The notice 28 describes that the different treatment is available at no cost to the patient and that there is a financial consequence of receipt of the treatment. In some examples of the invention, the notice will explain that the patient's employer has pre-paid for the different treatment. At least one benefit of such an example is that the example complies with HIPAA (standing for "Health Insurance Portability and Accountability Act of 1996, as amended), and proposed "wellness regulations."

According to at least one example, the treatment prescribed by the first care-giver comprises a drug. In at least some examples, the drug comprises at least one of the following:

| Tricyclic Antidepressants | Anxiolytic Hypnotics |
|---|---|
| Amitriptyline (Elavil) | Alprazolam (Xanax/Xanax XR) |
| Aventyl (Pamelor) | Clonazepam (Klonopin) |
| Clomipramine (Anfranil) | Clorazepate (Tranxene) |
| Desipramine (Norpramin) | Diazepam (Valium) |
| Imipramine (Tofranil) | Lorazepam (Ativan) |
| Nortriptyline (Pamelor) | Oxazepam (Serax) |
| Sinequan (Doxepin) | |
| Misc Antidepressants | Sedative Hypnotics |
| Bupropion (Wellbutrin/Wellbutrin SR/Wellbutrin XL) | Chloral Hydrate |
| | Estazolam (ProSom) |
| Duloxetine (Cymbalta) | Eszopiclone (Lunesta) |
| Mirtazapine (Remeron) | Flurazepam (Dalmane) |
| Nefazodone (Serzone) | Temazepam (Restoril) |
| Trazodone (Desyrel) | Triazolam (Halcion) |
| Venlafaxine (Effexor/Effexor XR) | Zaleplon (Sonata) |
| | Zolpidem (Ambien) |
| Non Benzodiazepine | SSRI |
| Buspirone (Buspar) | Escitalopram (Lexapro) |
| Vistaril (Atarax) | Citalopram (Celexa) |
| | Fluoxetine (Prozac/Serafem) |
| | Fluvoxamine (Luvox) |
| | Paroxetine (Paxil/Paxil CR) |
| | Sertraline (Zoloft) |
| MAOI | |
| Phenelzine (Nardil) | |
| Tranylcypromine (Parnate) | |

Other drugs, for other conditions, comprise the treatment prescribed by the first care-giver in still further examples (e.g., cholesterol drugs, medicine, blood thinners, insulin, and/or any other drug). In still further examples, the treatment prescribed by the first care-giver comprises surgery. Other treatments will occur to those of skill without departing from the invention.

In at least one example of the invention, covered participants who acquire certain identified medication using their prescription drug plan must contact an Employee Assistance Program ("EAP") (or Mental Health Management Vendor, a.k.a. "MHMV") or incur an increase in their co-pays for any of the listed medications. Once contact with the EAP or MHMV is made, the participant is provided an initial screening to determine if psychotherapy or other mental health services would assist with improving their condition. If it is determined that they would not benefit from the different treatment, the co-pay remains the same. If it is determined that they would benefit, they are offered a free referral to a licensed counselor through the EAP. If they accept the referral and participate in counseling and ongoing screenings to track outcomes and improvement, their co-pay for the identified medication is adjusted, in come situations, for a stated period of time. Employers may use either an incentive or penalty approach with this program by raising/lowering the participant's co-pay, dependent on compliance/non-compliance with the program. Additionally, in some examples, a financial incentive is offered to switch from a name brand to a generic prescription (if medically appropriate).

In at least some such examples, the majority of cases should be resolved under the EAP benefit, dependent of the session model (the greater the number of EAP sessions available, the greater the percentage resolved). Those needing treatment beyond the EAP are referred to the benefits under the health plan with the EAP coordinating all levels of care. The net result is reduced medical utilization, reduced drug costs, and a mentally healthy employee. In many examples of the invention, an employer is motivated to make additional treatment available to an employee due to the near term reduction in cost to the employer. First, when the notice is sent out, some of the employees will be non-compliant; and, therefore, the employer will pay less for the treatment prescribed by the first care-giver. Secondly, many of the different treatments, such as psychotherapy, rapidly reduce the amount of a drug the employee takes, again reducing the employer's cost. Third, many of the employees stop using the prescribed drug altogether. As a part of stopping use of the prescribed drug, a patient may be directed to an alternate, less expensive drug.

According to some further examples of the invention, active program promotion, legal and financial assistance, and an array of services for work/life (including: child care, elder care, adoption, schools, etc.) and wellness resources motivate additional participants to utilize the EAP. Supervisor training (e.g., on documentation and intervention for job performance issues) is also provided to enhance productivity and EAP utilization with impaired employees, in still further examples of the invention.

In many examples, the EAP is integrated with a self-funded health plan to create a mental health care management program. Through plan design, the EAP or MHMV is the "gatekeeper" for mental health and substance abuse benefits under the health plan. This integration is another process by which participants are motivated to access effective care, as they must contact the EAP before seeking treatment, or else they incur a reduction (or loss) of benefits for these issues. As a result, EAP utilization is increased along with the number of cases that are resolved under the EAP without utilizing the health plan benefits. For those requiring treatment beyond the EAP, the EAP care management department coordinates the treatment for each case utilizing a step-down approach. By authorizing successively less restrictive levels of treatment, as appropriate, not only are costs controlled but also positive outcomes are increased.

In some examples, the first care-giver comprises a physician, although, in further examples, the first care-giver comprises a medical professional other than a physician.

Referring still to FIG. 2, in many examples, at least one field 17 represents a treatment prescribed by the first care-giver. In some such examples, field 17 comprises a report from an insurance company or organization administering a self-insured health plan of treatments prescribed by the first care-giver, and the means 20 for determining compares a practice type of the physician prescribing a drug (e.g., obstetrics) to the type of drug prescribed (e.g., an antidepressant). The lack of a direct relation between the normal practice and the drug prescribed is a factor tending toward a determination that the patient would be eligible for different treatment, either in place of the drug or in parallel with it with the goal to avoid or lessen dependence on the drug.

In some examples of the invention, the example notice 28 comprises a writing 30, on a paper medium 31, including a description 32 of a cost saving for the treatment prescribed by the first care-giver; the cost savings is dependent upon participation by the patient in the different treatment. In some examples, the cost saving comprises a reduction in a cost in the event of participation by the patient in the different treatment (e.g., a reduction in a co-pay component of an insurance policy of the patient). In further examples, the notice 28 comprises a description 34 of a cost increase for the treatment prescribed by the first care-giver. As with the cost decrease, the cost increase is dependent upon lack of participation by the patient in the different treatment. In at least one such example, the cost increase comprises an increase in a cost in the event of failure by a patient to participate in the different treatment (e.g., an increase in a co-pay component of an insurance policy).

In at least some examples, such as seen in FIG. 2, the notice 28 further includes a description 36 of the different treatment. In some cases, the different treatment comprises counseling, and/or psychotherapy. In further examples, the different treatment comprises alternative drugs that, for example, have less addictive side effects than those prescribed by the first care-giver. In still further examples, the different treatment comprises alternative treatment such as prescribed exercise, neuromuscular therapy, and/or other "alternative" therapies.

Figure 3:
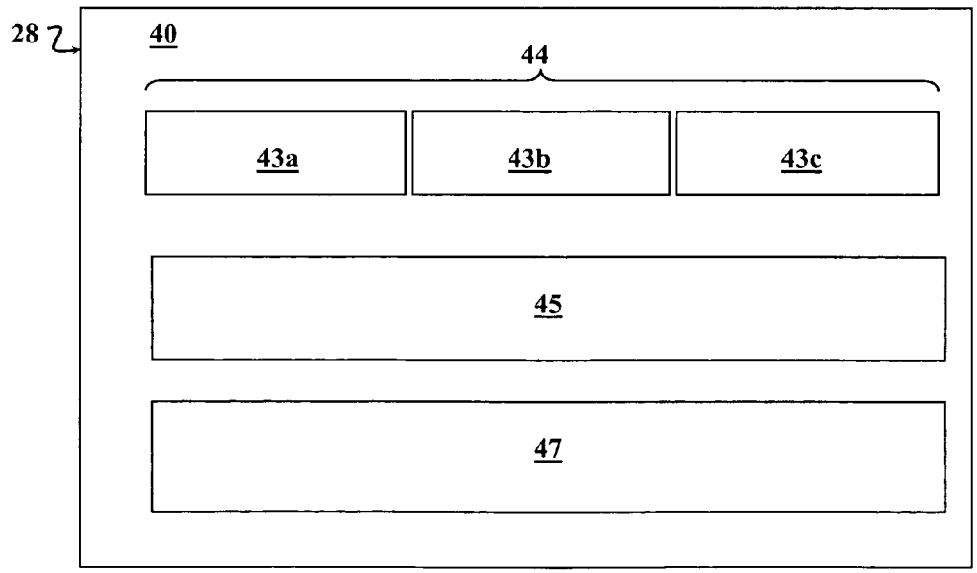
FIG. 3 is a top view of an example of the invention.

Referring now to FIG. 3, a further example of a notice 28 is seen in which a medium 40 (e.g., paper) includes a recordation of a set 44 of records 43a-43c. In at least one such example, the set 44 of records comprises: at least one record 43a representing a treatment prescribed by the first care-giver, and at least one record 43b representing at least one patient characteristic. The example of FIG. 3 also includes a recordation associated with the medium 40 of at least one field 45 associated an availability to a patient of a different treatment at no cost to the patient. Also seen is a further recordation of a field 47 that comprises, in this example, an explanation of a financial consequence of receipt or rejection of the different treatment.

Although the figures illustrate notice 28 as being in a paper medium, in alternative examples the medium comprises a set of signals encoded in any tangible or intangible manner or device capable of human perception, including volatile memory, screed displays (e.g., computers, PDAs, video terminals, thermal paper, etc.)

The above description is given by way of example only. Other examples will occur to those of skill in the art without departure from the spirit or scope of the invention, which is intended to be defined only by the claims below and their equivalents.

What is claimed is:

1. A process for decreasing the amount of treatment a patient requires from a first care-giver, the process comprising:
   receiving in a computer a set of records wherein the set of records comprises:
   at least one record representing a drug treatment prescribed by the first care-giver to said patient;
   wherein said drug treatment prescribed by the first care-giver comprises a psychotropic drug, and
   at least one record representing a medical specialty of the first care-giver;
   determining in the computer, from the set of records, and based on a predetermined set of screening criteria, whether a different treatment is available to said patient;
   wherein said determining is performed independently of records relating to effectiveness of the treatment prescribed for the patient by the first care-giver, and
   wherein said screening criteria comprises comparing the medical specialty of the first care-giver prescribing said drug treatment to the type of said drug treatment prescribed for said patient; and
   generating in the computer, in response to the determining, an eligibility tag associated with the patient;
   wherein said eligibility tag provides an indication that said different treatment is available for said patient; and
   wherein said generating an eligibility tag is performed if the medical specialty is not a mental health specialty and the type of said drug treatment is a psychotropic drug; and
   providing a notice to the patient associated with the eligibility tag of the different treatment availability;
   wherein the different treatment is provided at no cost to the patient; and
   wherein a financial consequence is described in the notice.

2. A process as in claim 1 wherein the treatment prescribed by the first care-giver comprises a drug chosen from the group consisting of: tricyclic antidepressants, anxiolytic hypnotics, non-benzodiazepines, bupropion, duloxetine, mirtazapine, nefazodone, trazodone, venlafaxine, sedative hypnotics, phenelzine, tranylcypromine, escitalopram, citalopram, fluoxetine, fluvoxamine, paroxetine, and sertraline.

3. A process as in claim 1 wherein the financial consequence described in the notice comprises a description of a cost saving for the drug treatment prescribed by the first care-giver, wherein the cost savings is dependent upon participation by the patient in the different treatment.

4. A process as in claim 3 wherein the cost saving comprises a reduction in a cost in the event of participation by the patient in the different treatment.

5. A process as in claim 4 wherein the reduction in a cost comprises a reduction in a co-pay component of an insurance policy.

6. A process as in claim 1 wherein the financial consequence described in the notice comprises a description of a cost increase for the drug treatment prescribed by the first care-giver, wherein the cost increase is dependent upon lack of participation by the patient in the different treatment.

7. A process as in claim 6 wherein the cost increase comprises an increase in a cost in the event of failure by the patient to participate in the different treatment.

8. A process as in claim 7 wherein the increase comprises an increase in a co-pay component of an insurance policy.

9. A process as in claim 1 wherein the different treatment comprises counseling.

10. A process as in claim 1 wherein the different treatment comprises psychotherapy.

11. A process as in claim 1 further comprising providing a monetary incentive to an employer to provide the different treatment at no cost to the patient.

12. A system for decreasing the amount of treatment a patient requires from a first care-giver, the system comprising:
   a computer comprising a processor and a memory configured to:
   receive a set of records wherein the set of records comprises:
   at least one record representing a drug treatment prescribed by the first care-giver to said patient;
   wherein said drug treatment prescribed by the first care-giver comprises a psychotropic drug, and
   at least one record representing a medical specialty of the first care-giver;
   determine, from the set of records, and based on a predetermined set of screening criteria, whether a different treatment is available to said patient;
   wherein said determining is performed independently of records relating to effectiveness of the treatment prescribed for the patient by the first care-giver, and
   wherein said screening criteria comprises comparing the medical specialty of the first care-giver prescribing said drug treatment to the type of said drug treatment prescribed for said patient; and
   a printer coupled to said computer and configured to:
   generate, in response to the determining, an eligibility tag associated with the patient;

wherein said eligibility tag provides an indication that said different treatment is available for said patient; and wherein said generating an eligibility tag is performed if the medical specialty is not a mental health specialty and the type of said drug treatment is a psychotropic drug; and provide a notice to the patient associated with the eligibility tag of the different treatment availability;

wherein the different treatment is provided at no cost to the patient; and wherein a financial consequence is described in the notice.

13. A system as in claim 12 wherein the treatment prescribed by the first care-giver comprises a drug chosen from the group consisting of: tricyclic antidepressants, anxiolytic hypnotics, non-benzodiazepines, bupropion, duloxetine, mirtazapine, nefazodone, trazodone, venlafaxine, sedative hypnotics, phenelzine, tranylcypromine, escitalopram, citalopram, fluoxetine, fluvoxamine, paroxetine, and sertraline.

14. A system as in claim 12 wherein the financial consequence described in the notice comprises a description of a cost saving for the drug treatment prescribed by the first care-giver, wherein the cost savings is dependent upon participation by the patient in the different treatment.

15. A system as in claim 12 wherein the financial consequence described in the notice comprises a description of a cost increase for the drug treatment prescribed by the first care-giver, wherein the cost increase is dependent upon lack of participation by the patient in the different treatment.

16. A system as in claim 12 wherein the different treatment comprises counseling.

17. A system as in claim 12 wherein the different treatment comprises psychotherapy.

18. A system for decreasing the amount of treatment a patient requires from a first care-giver, the system comprising:

means for receiving in a computer a set of records wherein the set of records comprises:

at least one record representing a drug treatment prescribed by the first care-giver to said patient;

wherein said drug treatment prescribed by the first care-giver comprises a psychotropic drug, and at least one record representing a medical specialty of the first care-giver;

means for determining in the computer, from the set of records, and based on a predetermined set of screening criteria, whether a different treatment is available to said patient;

wherein said determining is performed independently of records relating to effectiveness of the treatment prescribed for the patient by the first care-giver, and wherein said screening criteria comprises comparing the medical specialty of the first care-giver prescribing said drug treatment to the type of said drug treatment prescribed for said patient; and means for generating in the computer, in response to the determining, an eligibility tag associated with the patient;

wherein said eligibility tag provides an indication that said different treatment is available for said patient; and wherein said generating an eligibility tag is performed if the medical specialty is not a mental health specialty and the type of said drug treatment is a psychotropic drug; and means for providing a notice to the patient associated with the eligibility tag of the different treatment availability;

wherein the different treatment is provided at no cost to the patient; and wherein a financial consequence is described in the notice.

19. A system as in claim 18 wherein the financial consequence described in the notice comprises a description of a cost saving for the drug treatment prescribed by the first care-giver, wherein the cost savings is dependent upon participation by the patient in the different treatment.

20. A system as in claim 18 wherein the financial consequence described in the notice comprises a description of a cost increase for the drug treatment prescribed by the first care-giver, wherein the cost increase is dependent upon lack of participation by the patient in the different treatment.

* * * * *